United States Patent
Iwa et al.

(10) Patent No.: US 7,417,732 B2
(45) Date of Patent: Aug. 26, 2008

(54) PARTICLE MONITORING APPARATUS AND VACUUM PROCESSING APPARATUS

(75) Inventors: Yoichiro Iwa, Itabashi-ku (JP); Kazuhiro Miyakawa, Itabashi-ku (JP); Susumu Saito, Nirasaki (JP)

(73) Assignees: Kabushiki Kaisha TOPCON, Tokyo (JP); Tokyo Electron Limited, Tokyo (JP)

( * ) Notice: Subject to any disclaimer, the term of this patent is extended or adjusted under 35 U.S.C. 154(b) by 347 days.

(21) Appl. No.: 11/271,945

(22) Filed: Nov. 14, 2005

(65) Prior Publication Data

US 2006/0132769 A1 Jun. 22, 2006

Related U.S. Application Data

(60) Provisional application No. 60/636,487, filed on Dec. 17, 2004.

(30) Foreign Application Priority Data

Nov. 18, 2004 (JP) .............................. 2004-334759

(51) Int. Cl.
*G01N 15/02* (2006.01)
(52) U.S. Cl. ....................... 356/336; 356/335
(58) Field of Classification Search .......... 356/335–343
See application file for complete search history.

(56) References Cited

U.S. PATENT DOCUMENTS

| | | | | |
|---|---|---|---|---|
| 3,879,615 A * | 4/1975 | Moser | ......................... | 250/574 |
| 3,910,702 A * | 10/1975 | Corll | ............................ | 356/72 |
| 3,975,084 A * | 8/1976 | Block | .......................... | 356/335 |
| 4,906,094 A * | 3/1990 | Ashida | ........................ | 356/336 |
| 4,984,246 A * | 1/1991 | Cabaret et al. | ................. | 372/69 |
| 5,011,286 A * | 4/1991 | Petralli | ........................ | 356/343 |
| 5,092,675 A * | 3/1992 | Sommer | ..................... | 356/338 |
| 5,271,264 A * | 12/1993 | Chanayem | ................. | 73/28.01 |
| 5,317,380 A * | 5/1994 | Allemand | ................... | 356/338 |
| 5,481,357 A * | 1/1996 | Ahsan et al. | ................. | 356/338 |
| 5,654,797 A * | 8/1997 | Moreau et al. | .............. | 356/336 |
| 6,134,258 A * | 10/2000 | Tulloch et al. | ................ | 372/99 |
| 6,821,377 B2 | 11/2004 | Saito et al. | ............. | 156/345.24 |
| 6,896,764 B2 | 5/2005 | Kitazawa | ............... | 156/345.29 |
| 2003/0138021 A1 * | 7/2003 | Hodgson et al. | .............. | 372/75 |
| 2006/0078030 A1 * | 4/2006 | Altmann | ..................... | 372/69 |

FOREIGN PATENT DOCUMENTS

| | | | |
|---|---|---|---|
| GB | 2073412 A | * | 10/1981 |
| JP | 2000-77395 | | 3/2000 |
| JP | 2000-146819 | | 5/2000 |
| JP | 2003-229417 | | 8/2003 |

\* cited by examiner

*Primary Examiner*—L. G. Lauchman
*Assistant Examiner*—Jarreas C Underwood
(74) *Attorney, Agent, or Firm*—Oblon, Spivak, McClelland, Maier & Neustadt, P.C.

(57) ABSTRACT

A particle monitoring apparatus including a light source configured to emit plural light fluxes, a projecting optical system configured to convert the plural light fluxes into a band-shaped light flux, to lead the band-shaped light flux into a flow passage of a given gas stream, and to partially superpose the plural light fluxes to form a substantially uniform light intensity distribution of the band-shaped light flux in a widthwise direction; a light detector configured to detect intensity of light; and a particle detector configured to determine sizes of the particles passing the light flux based on intensities of the scattered lights detected by the light detector and to count the number of the particles.

10 Claims, 5 Drawing Sheets

PARTICLE MONITORING APPARATUS AND VACUUM PROCESSING APPARATUS

BACKGROUND OF THE INVENTION

1. Field of the Invention

The present invention relates to a particle monitoring apparatus configured to be arranged in a so-called clean room or the like, mainly in a vacuum processing apparatus in a semiconductor producing process line or the like and to monitor sizes and number of particles ("dust" so-called particles, etc.) in a gas stream. The invention also relates to a vacuum processing apparatus equipped with the particle monitoring apparatus. More particularly, the invention relates to an improvement on the gas-bonre particle monitoring apparatus configured to determine the sizes of the particles depending upon the intensities of the lights scattered by the particles.

2. Related Art Statement

In the semiconductor producing process line, for example, particles are heretofore removed to a high level, while the number and sizes of the remaining particles are constantly being monitored.

A particle counter (particle monitoring apparatus) has been known to monitor such particles (contamination/supernatant). The particle counter is arranged inside an exhausting section of a processing apparatus in the semiconductor producing process line, for example.

When the gas stream in the process, which flows into the exhausting section, passes a light beam (light flux) shaped in a sheet-like (band-like) form, any particles contained in the gas stream scatter the light. Therefore, presence of the particles can be detected by sensing the scattered light (Patent literature 1: JP-A 2000-146819).

It is known that there is a specific correlation between the intensity of the detected scattered light and the size of the particle. Thus, if the correlation between the sizes of the particles and the intensities of the scattered lights is empirically determined in advance, the sizes of the particles can be determined based on the detected intensities of the scattered lights in actual use.

Further, the particle counter monitors the cleanness state inside the dry etching apparatus by countering the number of particles for each of the discriminated sizes of the particles.

When the correlation between the sizes of the particles and the intensities of the scattered lights is to be determined in advance, test particles having known sizes (PSL: Polystyrene Latex) are used.

On the other hand, it is laterally inhomogeneous that the projected light intensity distribution of the band-shaped light beam formed with the conventional particle counter. The band shape of the projected light intensity distribution in the horizontal direction of the laser beam is Gauss distribution. And, it is identified not a function mode (TEM00: Transverse Electromagnetic 00) but a multimode in the propagating characteristic that Gauss distribution of a light induced through a multimode-fiber with a projected light system.

According to any conventional particle counter, the widthwise central portion of the light beam has the highest light intensity, and the light intensity decreases as the location goes from the center toward a widthwise edge portions of the light beam.

Therefore, the intensity of the scattered light obtained when the particle passes the widthwise central portion of the band-shaped light beam is different from that of the scattered light obtained when the particle passes near the widthwise edge portion of the band-shaped light beam, even if the size of the former particle is identical with that of the latter one. The intensity of the scattered light obtained when the particle passes the widthwise central portion of the band-shaped light beam is greater than that of the scattered light obtained when the particle passes near the widthwise edge portion of the band-shaped light beam.

For this reason, when the size of the particle is determined based on the detected intensity of the scattered light, it is feared that a considerable error is contained in the determined value.

When the correlation between the sizes of the particles and the detected intensities of the scattered lights is to be determined in advance, the intensities of the scattered lights are repeatedly detected by using the test particles having the same size, or the intensities of the scattered lights are detected by using a number of the test particles determined corresponding to said size based on the frequency distribution of the detected intensities of the scattered lights. However, since the intensity of the scattered light depends upon the passing position of the particle through the light beam as mentioned above, a peak among the frequencies is not clear. Consequently, there is a problem in that the correlation between the sizes of the particles and the intensities of the scattered lights cannot be accurately set.

SUMMARY OF THE INVENTION

The present invention has been accomplished in view of the above problems, and its object is to provide a particle monitoring apparatus which can prevent or reduce variations in the detected intensities of the scattered lights depending upon their passing locations of the particles through a gas stream passage area and can thereby enhance accuracy of detecting the sizes of the particles.

Another object of the present invention is aimed at the provision of a vacuum processing apparatus equipped with the above particle monitoring apparatus. In the vacuum processing apparatus to be used in the semiconductor producing or processing process line or the like, it is particularly important to appropriately monitor the above-mentioned particles.

According to the particle monitoring apparatus of the present invention, the band-shaped light flux through which the gas stream passes is formed to have an almost uniform light intensity distribution in the horizontal direction. Consequently, the dependency of the in the horizontal direction. Consequently, the dependency of the intensities of the lights upon the locations can be prevented or reduced, so that the correlation between the detected intensities of the scattered lights and the sizes of the particles can be enhanced.

That is, a first particle monitoring apparatus according to the present invention comprises a light source configured to emit a light having a given intensity, a projecting optical system configured to converting the light emitted from the light source into a band-shaped light flux and to lead the light flux onto a flow passage of a given gas stream so that the given gas stream may pass the band-shaped light flux, a light detector configured to detect the intensity of the light, a detecting optical system configured to lead the light scattered by particles contained in the gas stream and passing the light flux to the light detector, and a particle detector configured to determine sizes of the particles passing the light flux based on intensities of the scattered lights detected by the light detector and to count the number of the particles passing the light flux for a given period, wherein the light intensity of the band-shaped light flux is set to have an almost uniform distribution in a horizontal direction.

Herein, the given gas stream is a gas stream flowing mainly in a constant direction (and not flowing back), such as a gas stream to be exhausted through an exhausting section of the processing apparatus like a clean room in the semiconductor processing line.

As to "almost uniform light intensity distribution (projected light intensity) in the band-widthwise direction of the light flux, the light flux needs only to be almost uniform at least in a range where the gas stream passes (gas stream-passing area), but this light intensity needs not be accurately uniform up to edge portions in the widthwise direction.

The uniformity of the intensity of the projected light can be attained by partially superposing plural light fluxes, for example. At that time, the plural light fluxes may be obtained by simultaneously emitting the plural light fluxes from a single light source or simultaneously and independently emitting the plural light fluxes from plural light sources, respectively.

A single light flux emitted from a single light source may be divided into plural light fluxes by means of the projecting optical system. Since plural light fluxes need not be emitted from a single light source, the invention is advantageous from the standpoint of the cost and procurement of the light source.

However, when the emitted light flux is a laser flux having high coherency, light fluxes (divided light fluxes) obtained by dividing the single light flux may interfere with each other or one another if their phases are aligned with each other or one another. Thus, there is the possibility that any inconvenience can occur when the divided light fluxes are partially superposed.

Under the circumstances, if such a light flux having strong coherency is to be used, it may be that a single light flux separately emitted from each of two light sources, for example, is divided, and a divided light flux of one light source is made adjacent to a corresponding divided light flux of the other light source, and partially superposed thereupon, while the divided light fluxes from each of the light source are not adjacent to each other.

In case that the plural light fluxes are partially superposed with each other by means of the projecting optical system, it may be that the plural light fluxes are separately collimated by the same number of lenses as that of the plural light fluxes, respectively, long distances between the gas stream-passing area and the plural lenses are ensured, and the fluxes are defocused to partially superpose the light fluxes with each other. Alternatively, the plural light fluxes are passed through different portions of a single lens (different portions as viewed in radial directions orthogonal to the optical axis of the lens), and thereby the resulting light fluxes having independently small open angles are obtained and then are partially superposed while distances between the light sources and the gas passing area and distances between the single lens and the gas stream passing area are adjusted.

According to the thus constructed particle monitoring apparatus, since the intensity of the projected light is almost uniform in the horizontal direction (band-width direction) in the gas stream passing area. Therefore, even if the particles pass any location in the widthwise direction of the gas stream passing area, the detected intensity of the light scattered by the passed particle is constantly uniform when the respective sizes of the particles are identical. As in the case with the conventional cases, the intensity of the projected light can be regarded almost identical in the light-advancing direction.

Thus, dependency of the detected intensity of the scattered light in the gas stream passing area upon the passing location (position in the light-advancing direction and the position in the band-widthwise direction) is prevented or reduced, so that the correlation between the detected intensities of the scattered lights and the sizes of the passed particles can be enhanced. Thereby, the sizes of the passed particles having passed the band-shaped light flux can be determined with higher accuracy based on the detected intensities of the scattered lights.

Further, when the number of passed particles per each size is to be countered, that number of the particles can be counted with high accuracy per each size, because the accuracy of discriminating the sizes of the particles is high.

The above-mentioned light flux is preferably a laser beam in that the laser beam has excellent directional characteristic. In the following, the laser beam is also preferable in each of the particle monitoring apparatuses according to the present invention.

In the particle monitoring apparatus of the present invention, it is preferable that the light source is preferably a light source configured to emit plural light fluxes in at least one-dimensional array, and that the projecting optical system is configured to partially superpose the light fluxes emitted from the light source so that the light intensity distribution in a widthwise direction of the band-shaped light flux may be almost uniform.

The plural light fluxes are arrayed in a direction corresponding to the widthwise direction of the band-shaped light flux in the gas stream passing area. Further, partial superposition of the light fluxes means that the light fluxes are superposed upon each other in the arrayed direction. The plural light fluxes may be emitted from a single light source or from plural light sources, respectively.

According to the thus constructed particle monitoring apparatus, the light flux having the almost uniform projected light intensity in the band-widthwise direction can be easily formed by the construction in which the light source emits the plural light fluxes in a one-dimensional array and the projecting optical system partially superpose the light fluxes thus emitted.

In the particle monitoring apparatus according to the present invention, the projecting optical system preferably comprises plural optical systems provided in a number corresponding to that of the plural light fluxes emitted from the light source and adapted for leading the plural light fluxes, respectively.

According to the thus constructed particle monitoring apparatus, since the optical systems are provided corresponding to the respective light fluxes, variations in each of the light fluxes emitted from the light source can be independently adjusted, so that adjustment can be easily made to attain the uniform intensity of the projected light in the gas stream passing area.

Further, it is preferable in the particle monitoring apparatus according to the present invention that the light source comprises at least two light sources, and that the projecting optical system is configured to divide the light flux emitted from each of the light sources into plural light fluxes, to make divided light fluxes (light fluxes obtained by dividing the light flux) of one light source adjacent to those of corresponding different light source(s) to partially superpose the adjacent divided light fluxes with each other and to make almost uniform the light intensity distribution of the band-shaped light flux in the band-widthwise direction.

According to the thus constructed particle monitoring apparatus, even if the light fluxes emitted from the light sources are the laser fluxes or the like having high coherency, there hardly occurs interference between the light fluxes originating from each light source. Thus, when the projecting optical system divides the single light flux emitted from each of at least two light sources, makes a divided light flux of one light source adjacent to those of corresponding different light source(s) and partially superposes the adjacent divided light fluxes with each other, while the divided light fluxes originated from the same light source is prevented from being adjacent to each other, the intensity distribution of the projected light in the gas stream passing area can be made uniform.

Since each light source has only to emit a single light flux, such can be prepared at a lower cost as compared with the light source to emit plural light fluxes, the former is advantageous from the standpoint of the manufacturing cost.

It is preferable in the particle monitoring apparatus of the present invention that the particle detector comprises a memorizing unit configured to preliminarily memorize correlation between the sizes of the particles passing the gas stream passing area and the intensities of the scattered lights detected by the light detector, and the correlation memorized in the memorizing unit is defined by successively passing plural kinds of test particles each having a different known size through the gas stream passing area, independently detecting the intensities of the scattered lights with the light detector when each of the plural kinds of test particles passed the gas stream passing area, determining the frequency distribution in the light intensities detected by the light detector, determining the correlation between the size of each of the plural kinds of the particles and the detected light intensities of the scattered lights by the particles having such sizes based on the frequency distribution, replacing one kind of the test particles by another of the test particles having a known different size and passing them through the gas stream passing area and determining the intensities of the scattered lights when these test particles passed, and determining the correlation between the size of another type of the test particles and the detected light intensities of the scattered lights, and repeating the above latter step.

According to the thus constructed gas particle monitoring apparatus, since a reference table (look-up table) defining the correlation between the sizes of the particles and the intensities of the scattered lights, a threshold intensity value for discriminating the sizes of the particles or the like is memorized in the memorizing unit provided in the particle detector, the corresponding size of the particle can be specified, in actual use, based on the detected intensity of the scattered light by referring to the correlation memorized in the memory unit.

As to the correlation memorized in the memorizing unit, the sizes of the particles are correlated with the intensities of the scattered lights as follows. That is, the frequency distribution (histogram) in the scattered light intensity is obtained by using a number of the test particles having the known size, the intensity of the scattered light exhibiting the largest frequency is correlated with that size based on the histogram, for example, or the intensities of the scattered lights are extracted corresponding to the frequencies fallen in a range of 80% or more of the largest frequency, products between the extracted intensities of the scattered lights and the corresponding frequencies are calculated, and the weighted average of the intensity of the scattered light, which is obtained by dividing each of products with a sum of the corresponding frequencies is correlated with the size. The distribution of the light intensities in the gas stream-passing area is uniform at the time of preliminarily detecting the intensities of the scattered lights. Thus, the intensities of the scattered lights detected through passage of a number of the test particles having the identical size are almost constant. Accordingly, the above-mentioned frequency distribution exhibits a distribution in which the specific intensities of the scattered lights have the concentrated frequency.

Therefore, the intensity of the scattered light can be easily specified corresponding to the size of the particle one-on-one with high probability and accuracy.

Thus, since the size of the particle is determined in actual use based on the thus accurately specified correlation, the size of the particle can be precisely determined with high accuracy.

A particle monitoring apparatus according to a second aspect of the present invention comprises a light source configured to emit a light having a predetermined intensity, a projecting optical system configured to convert the light emitted from the light source into a band-shaped light flux and to lead the band-shaped light flux onto a flow passage of a given gas stream so that the given gas stream may pass the band-shaped light flux, a light detector configured to detect the intensity of the light, a detecting optical system configured to lead the light scattered by particle contained in the gas stream and passing the light flux to the light detector, and a particle detector configured to determine a size of the particle passing the light flux based on intensity of the scattered light detected by the light detector, wherein the light intensity of the band-shaped light flux (the intensity of the projected light) is set to have an almost uniform distribution in a horizontal direction.

According to the thus constructed particle monitoring apparatus, since the intensity of the projected light is almost uniform in the widthwise direction (band-widthwise direction) in the gas stream passing area. Therefore, even if the particles pass any location in the widthwise direction in the gas stream passing area, the detected intensity of the light scattered by the passed particles is constantly uniform when the respective sizes of the particles are identical. As in the case with the conventional cases, the intensity of the projected light can be regarded almost identical in the light-advancing direction.

Dependency of the intensity of the scattered light detected in the gas stream passing area upon the passing location (position in the light-advancing direction and position in the band-widthwise direction) is avoided or reduced, so that the correlation between the detected intensities of the scattered lights and the sizes of the passed particles can be enhanced. Thereby, the sizes of the passed particles can be determined with high accuracy based on the detected intensities of the scattered lights.

Further, the vacuum processing apparatus according to the present invention, which is to perform a given processing upon an object disposed in a given vacuum atmosphere inside a vessel, comprises any of the particle monitoring apparatuses mentioned above.

Herein, as the vacuum processing apparatus, an etching apparatus, a sputtering apparatus, a thermal CVD device, etc. may be recited as typical examples. The vacuum processing apparatus may include various kinds of vacuum processing apparatuses used in semiconductor producing process line, such as plasma etching apparatus, plasma CVD apparatus, RTP (rapid/thermal processing) apparatus, annealing apparatus, ashing apparatus, oxide film-forming apparatus, thermally processing apparatus and the like as disclosed in JP-A 03-22941, JP-A 2000-077395, etc.

Besides the above particle monitoring apparatus, the vacuum processing apparatus may adopt a specific construction comprising a processing chamber (container) to be sucked to vacuum, a mounting table, a gas feeder, an exhausting system with a vacuum pump. The mounting table is placed inside the processing chamber for placing an object (a semiconductor wafer, a glass substrate or the like to be used in a LCD (for example, liquid crystal display) substrate or FPD (flat panel display)) to be subjected to a given processing such as the above etching or a sputtering, substrate. The gas feeder is configured to feed a gas necessary for the above processing into the processing chamber for performing the above processing. The exhausting system is configured to convert the atmosphere inside the vacuum chamber to a vacuum state (vacuum sucking) (meaning not only a completely vacuum state but also a low pressure state being lower than the atmospheric pressure but suitable for the above processing).

According to the particle monitoring apparatus of the present invention provided in the thus constructed vacuum processing apparatus, the projecting optical system is arranged to convert the light flux emitted from the light source into the band-shaped light flux, and leads the light flux toward the gas stream passing a flow passage of the exhausting system.

Although the pressure is very low inside the vacuum chamber, the above-mentioned particle monitoring apparatus can monitor "the particles in the gas stream" inside the vacuum chamber, because the gas stream is generated by vacuum sucking with the exhausting system. During when the above specified processing is being performed by the vacuum processing apparatus, the predetermined gas is introduced into the vacuum processing chamber by the gas feeder, and this gas passes the flow passage of the exhausting system. Thus, the gas forms the gas stream to be monitored.

The vacuum processing apparatus according to the present invention preferably further includes a control unit for controlling the operation of the vacuum processing apparatus based on the monitored result of the particle monitoring apparatus. When the controller performs control of changing the operation contents of the vacuum processing apparatus or stopping the operation itself, for example, based on the monitored result of the particle monitoring apparatus, the operation state in which the monitored result with the particle monitoring apparatus is appropriately reflected can be realized.

It goes without staying that the above controller may be obtained by additionally affording the above function of controlling the operation based on the above monitored results upon such a controller as is conventionally provided in the vacuum processing apparatus for controlling the operation of the gas feeder or the exhausting system.

Since the thus constructed vacuum processing apparatus according to the present invention is equipped with the invented particle monitoring apparatus, the former can enjoy the functions and effects themselves exhibited by the latter as they are. Thus, the accuracy of detecting the particles can be enhanced to make the processing with the vacuum processing apparatus more appropriate.

The vacuum processing apparatus is broadly constituted by a processing chamber where the object is processed with the processing gas, and the exhausting system for exhausting air and the processing gas inside the processing chamber as well as the particle monitoring apparatus (particle counter) for measuring the sizes of the particles in an exhaust gas (gas stream) flowing in the exhausting system and counting the number of those particles.

This particle monitoring apparatus comprises a main body, and a controlling/processing unit (for example, controller) for controlling the operation of the main body. The controlling/processing unit may be assembled into the control unit of the vacuum processing apparatus or may be separately provided therefrom.

The system controller of the vacuum processing apparatus controls the operations of the vacuum processing apparatus and the particle monitoring apparatus for controlling the entire processing process from an operation in which a substrate such as a semiconductor wafer as the object to be processed by the vacuum processing apparatus is transferred inside the vacuum processing apparatus to an operation in which the object is carried outside.

If the vacuum processing apparatus is to be cleaned to remove particles inside the apparatus, monitored results (for example, the detected number of the particles and the detected sizes of the particles) with the particle monitoring apparatus are inputted into the control unit of the vacuum processing apparatus, and the inputted monitored results are subjected to assay and analysis based on mathematically statistic processing or the like with an APC control system (not show), thereby calculating a cleaning condition fit for the processing process.

The APC control system determines a particle-removing motion according to the calculated cleaning condition, and outputs the determined result to the control unit, which makes control to terminate the particle-removing operation upon receipt of an order of the determined result.

The control unit may receive the signal for the termination of the cleaning from the APC control system, and control an operation for opening or closing a gas on/off valve in the gas feeder or a high frequency input-terminating timing, for example.

The control unit controls the entire operation of the vacuum processing apparatus, and can manage statistical steps through being connected to a host server computer or the APC control system via a network.

A control system may be provided, in which control parameters are incorporated in advance. As these parameters, at least one IM (Integrated Metrology) means for measuring the film pressure, the pressure, the concentration and components of the processing gas, the film quality, the CD, etc. is provided inside the processing apparatus or in a bay of the semiconductor-producing line, thereby performing the optimum processing (semiconductor-processing).

Hereinbefore, the operation of the particle monitoring apparatus during cleaning has been explained. The monitoring apparatus can be also used to detect the cleanness degree inside the processing chamber before the processing process or to monitor the particles during the processing step.

The point of time when the number of the particles is decreased to around a few to several is almost a point of time of just etch in the processing process. Thus, this point of time can be automatically detected so that the point of termination of the processing process may be determined based on the detected point of time.

According to the particle monitoring apparatus of the present invention, since the intensity of the projected light is almost uniform in the horizontal direction (band-width direction) of the band-shaped light flux in a place where the gas stream passes, the intensity of the scattered light detected when the particle passes at an arbitrary location in the widthwise direction takes almost a constant value. That is, dependency of the detected intensity of the scattered light upon the particle-passing position in the widthwise direction can be avoided or reduced.

The light intensity distribution in the light-advancing direction is regarded more uniform than conventionally.

Therefore, the light intensity distribution in the gas stream passing area is almost uniform both in the light-advancing direction and in the band-width directiton.

Thereby, the dependency of the intensity of the scattered light detected when the particle passes the band-shaped light flux upon the passing location (the position in the light-advancing direction and the position in the band-widthwise direction) can be avoided or reduced. Thus, the correlation between the detected intensity of the scattered light and the size of the passed particle can be enhanced, so that the size of the particle having passed the band-shaped light flux can be accurately determined according to the detected intensity of the scattered light.

It is preferable in the vacuum processing apparatus of the present invention that the processing with the vacuum processing apparatus can be made more appropriate by enhancing the detection accuracy for the particles.

BRIEF DESCRIPTION OF THE DRAWINGS

For a better understanding of the invention, reference is made to the attached drawings, wherein:

FIGS. 4(a) and 4(b) show figures illustrating discriminating ability based on frequency distribution in intensities of scattered lights corresponding to sizes of particles, FIG. 4(a) being histograms for 0.100 μm and 0.107 μm, respectively, and FIG. 4(b) being histograms for 0.294 μm and 0.309 μm, respectively.

BEST MODE FOR CARRYING OUT THE PRESENT INVENTION

Figure 1:
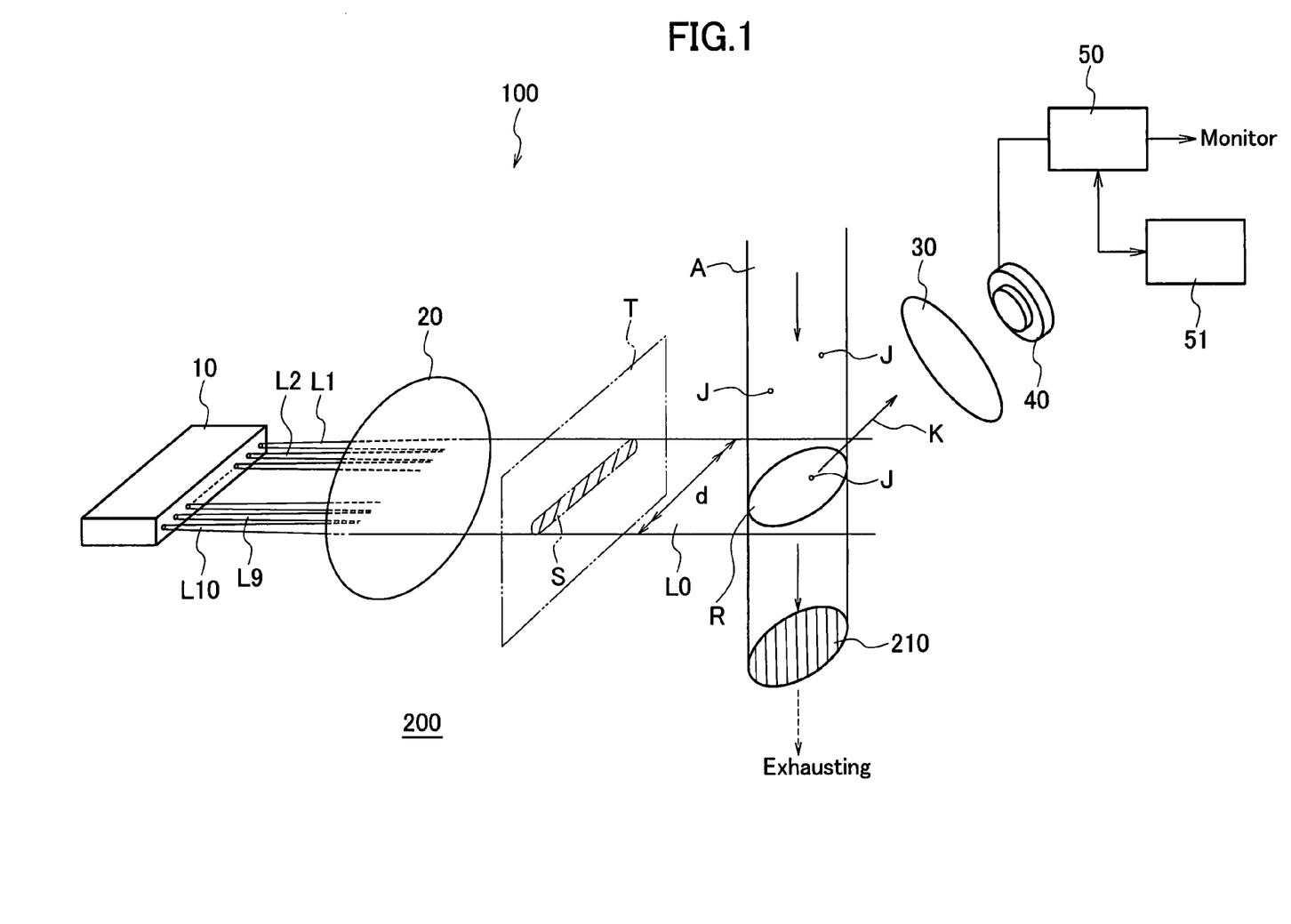
FIG. 1 is a figure showing the construction of a particle counter (particle monitoring apparatus) according to one embodiment of the present invention.

In the following, best modes of the particle monitoring apparatus and the vacuum processing apparatus will be explained with reference to the drawings. FIG. 1 is a figure showing an outlined structure of a particle counter 100 as one embodiment of the particle monitoring apparatus according to the present invention.

The illustrated particle counter 100 is arranged in a semiconductor-processing process line 200 delimited from an outer space, and comprises a laser source 10, a projecting optical system 20, a detecting optical system 30, a light receiver 40 (light detector), and a particle detector 50. The laser source 10 emits ten laser fluxes L1, L2, - - - , L10 arranged in a one-dimensional fashion. The projecting optical system 20 converts ten light fluxes L1, - - - , L10 emitted from the laser source 10 in one straight line to a single band-shaped light flux LO (in a band-widthwise direction "d") as a whole, and leads the light flux LO through a flow passage for a gas stream A flowing toward an exhaust outlet 210 of the processing apparatus in the semiconductor processing unit 200 so that the gas stream A may pass the band-shaped light flux LO almost orthogonally in the widthwise direction "d". The detecting optical system 30 leads, to the light receiver 40, a scattered light scattered, at a given angle (angle other than integer time(s) of 180°) relative to the advancing direction of the light flux LO, by a particle "J" contained in the gas stream A and passing the light flux LO. The light receiver 40 (light detector) detects the intensity of the light. The particle detector 50 determines the sizes of particles "J" passing the light flux LO based on the intensities of the scattered lights K detected by the light receiver 40 and counts the number of the particles "J" having passed the light flux LO with respect to each of the sizes during a given time period (time interval). The particle detector 50 comprises a memory 51 (memorizing unit) in which the correlation between the intensities of the scattered lights K detected by the light receiver 40 and the sizes of the particles J passing the area R through which the gas stream A passes in the band-shaped light flux LO (hereinafter referred to as the "gas stream-passing area") is stored in advance.

Herein, the projecting optical system 20 is configured to partially superpose ten laser fluxes L1, - - - , L10 emitted from the laser source 10 such that the light intensity of the band-shaped light flux LO may be almost uniformly distributed in the band-widthwise direction "d" in the gas stream passing area R. More specifically, ten laser fluxes L1, - - - , L10 are passed through respectively different portions (different portions as viewed in radial directions of the lens orthogonal to the optical axis thereof) of a single lens constituting a part of the projected light optical system 20 to convert them into light fluxes each having a small open angle, so that the laser fluxes L1, - - - , L10 are partially superposed upon another by adjusting the distance between the laser source 10 and the gas stream passing area "R" and the distance between the single lens and the gas stream passing area "R".

Figure 3A:
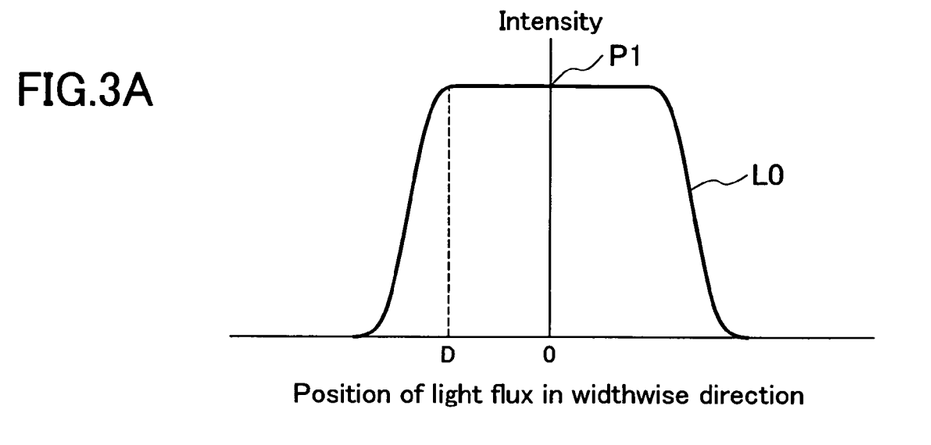
FIGS. 3(a) and 3(b) show figures of intensity distributions of projected lights, FIG. 3(a) being a figure for the embodiment shown in FIG. 1 and FIG. 3(b) being one for the conventional example.

As shown in FIG. 3(a), the light intensity distribution in the widthwise direction "d" of the band-shaped light flux LO is an almost uniform intensity P1 in a sectional face S taken by an imaginary plane T orthogonal to the advancing direction of the light flux LO. That is, the intensity is P1 both in the central portion and in a portion apart from the center by a distance D in the widthwise direction "d", so that the intensity distribution is not dependent upon the locations.

Figure 2A:
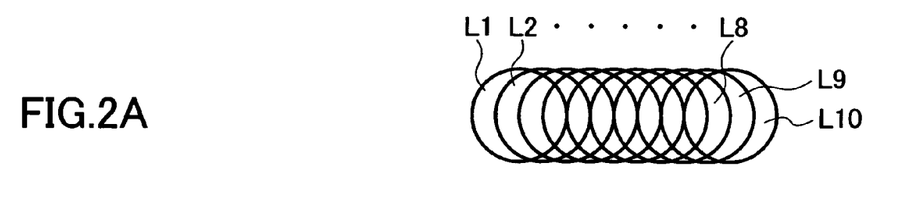
FIGS. 2(a) to 2(d) show figures of a projected light in the particle counter shown in FIG. 1, FIG. 2(a) being a figure showing contours drawn for respective emitted light fluxes as viewed in cut sections S, FIG. 2(b) being a figure showing an intensity distribution of each of the ejected light fluxes, FIG. 2(c) being a figure in which the fluxes in FIG. 2(a) are combined together, and FIG. 2(d) being a figure in which the intensity distributions in FIG. 2(b) are combined together.
Figure 2B:
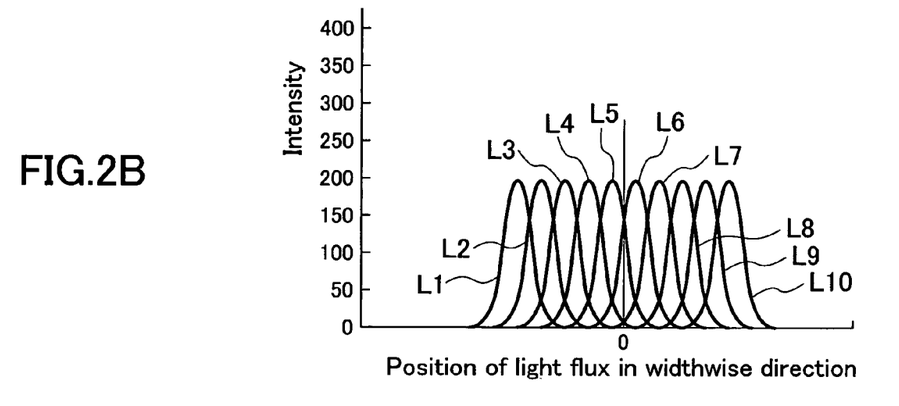
Figure 2C:
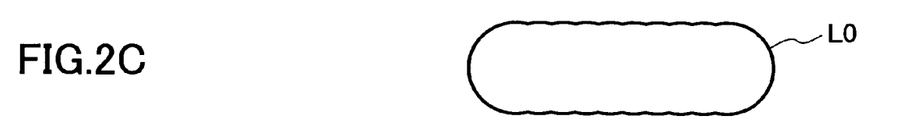
Figure 2D:
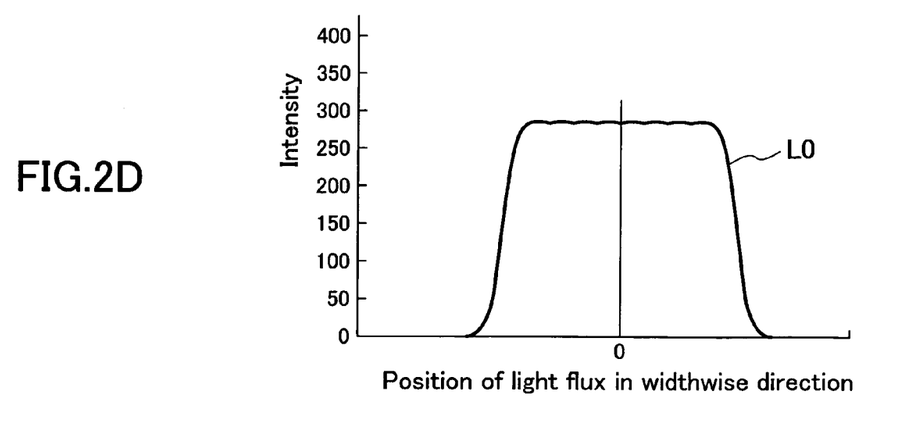
Figure 3B:
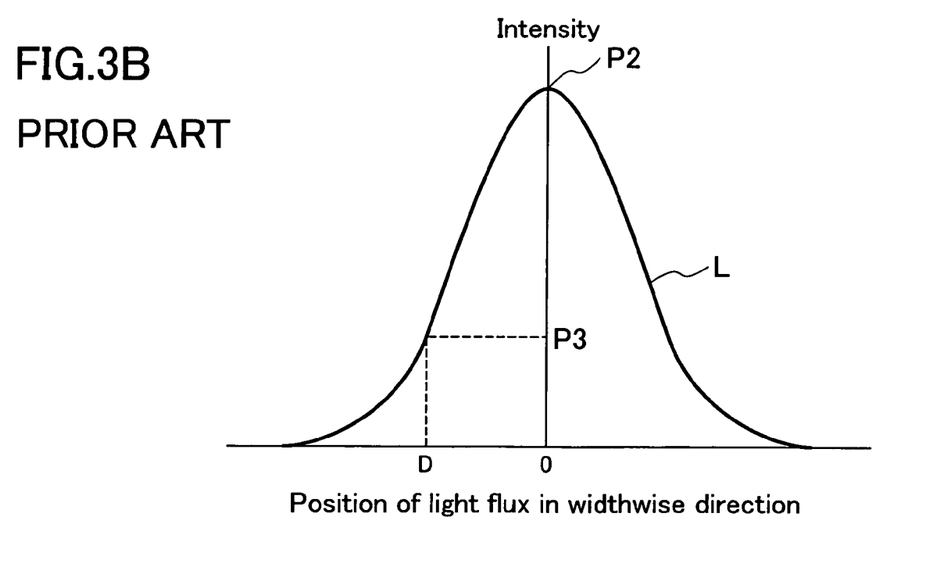

The light flux LO apparently has a contour shown in FIG. 2(c) in the sectional face S, the counter being obtained by partially superposing, in the sectional plane S as shown in FIG. 2(a), the laser fluxes L1, - - - , L10 each singly exhibiting a Gauss distribution in the sectional face as shown in FIG. 2(b). As shown in FIG. 2(d) (identical with FIG. 3(a)), the light flux LO has an intensity distribution in which intensities are added in relation to the locations in the widthwise direction "d". The light intensity distribution shown in FIG. 3(b) is an intensity distribution of the projected light in the gas stream passing area R determined by the conventional particle counter. The light is the projected light formed by a single light flux, which exhibits a Gauss distribution as shown. Therefore, The intensity is P2 in a central portion in the widthwise direction "d", whereas the intensity in a portion apart from the center by a distance D is P3 far smaller than P2. Thus, the light intensity largely depends upon the locations.

The particle detector 50 determines the size of the particle J penetrating the light flux LO based on the intensity of the scattered light K detected by the light receiver 40. The size of the particle J is determined by the following function.

That is, the correlation between the sizes of the particles J passing the gas stream passing area R and the intensities of the scattered lights K detected with the light receiver 40 is empirically determined in advance, and the thus determined correlation is memorized in the memory 51 as a reference table or a threshold value to discriminate given size ranges of the particles. Thus, the particle detector 50 can determine the size of the particle J corresponding to the detected intensity of the scattered light by referring to the reference table memorized in the memory 51 or by comparing and correlating the detected intensity of the scattered light K with the threshold value memorized in the memory 5.

How to set the correlation between the intensities of the scattered lights memorized in the memory 51 and the sizes of the particles J will be concretely explained below.

First, a number of PSL particles (test particles) all having the same known size are successively passed, instead of particles J in an actually use, through a given gas stream passing area R in the same manner as actually used, the light intensity of the scattered light K formed when each PSL particle passes the gas stream passing area R is independently detected, and histograms are formed for the intensities of the scattered lights detected by the light receiver 40.

With respect to a number of the PSL particles all having another same size (known), a histogram is similarly formed.

Figure 4A:
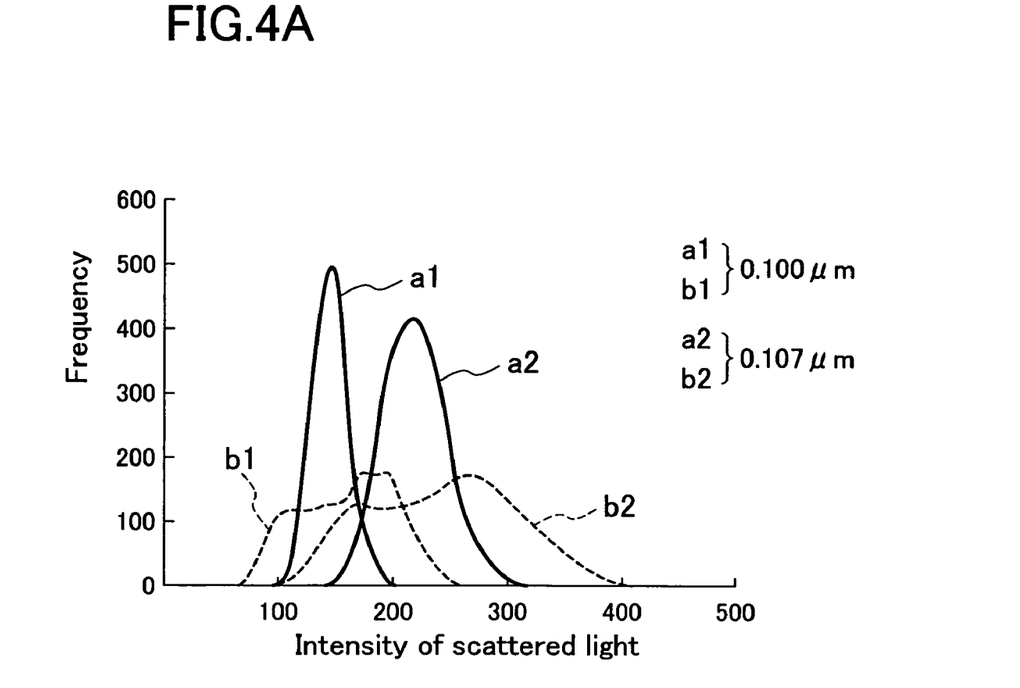

For example, the PSL particles having the size (diameter) of 0.100 µm and the PSL particles having the size (diameter) of 0.107 µm give two histograms obtained in FIG. 4(a). In FIG. 4(a), the frequency distribution "a1" corresponds to the diameter 0.100 µm, whereas the frequency distribution "a2" corresponds to the diameter 0.107 µm. The frequency distributions b1 and b2 obtained by the conventional particle counter correspond to the frequency distributions a1 and a2, respectively.

With respect to the thus obtained frequency distribution "a1", the sizes are correlated with the intensities of the scattered lights as follows. That is, the intensity of the scattered light exhibiting the maximum frequency is correlated with the size (diameter). Alternatively, the intensities of the scattered lights corresponding to not less than 80% of the maximum frequency are extracted, and products between the intensities of the extracted scattered lights and the corresponding frequencies are calculated, the weighted average of the intensities of the scattered lights obtained by dividing the products with the determined by the total of the corresponding frequencies is correlated to the corresponding size (0.100 µm).

Herein, with respect to the frequency distribution "a2", the size (diameter: 0.107 µm) is similarly correlated to the intensity of the scattered light.

Comparison of the frequency distribution "a1" determined by the particle counter of the present embodiment with that "b1" by the conventional particle counter reveals that the former has a higher and clearer peak of the frequency and a narrower range of the intensities of the scattered lights.

Same is applicable to comparison between the frequency distributions "a2" and "b2" in that the particle counter of the present embodiment gives an extremely clearer correlation between the size of the PSL particle and the intensity of the scattered light as compared with the conventional particle counter. As a result, the intensity of the scattered light corresponding to the size of 0.100 µm (frequency distribution "a1") is more clearly discriminated from that corresponding to the size of 0.107 µm (frequency distribution "a2") as compared with the conventional case.

Figure 4B:
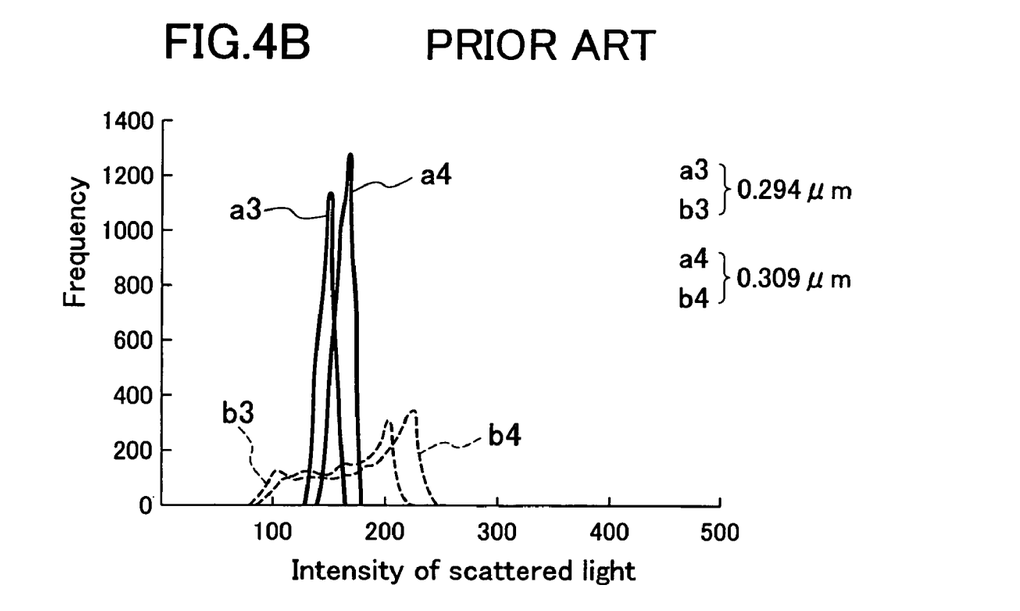

FIG. 4(b) shows a histogram for the PSL particle having the size (diameter) of 0.294 µm and that for the PSL particle having size of 0.309 µm, while the condition being varied. The PSL particles having these sizes exhibited extremely clearer correlation between the size of the PSL particle and the intensity of the scattered light as compared with the frequency distribution b3 (size: 0.294 µm) and the frequency distribution "b4" (size: 0.309 µm) in the case of the conventional particle counter. As compared with the conventional case, the intensities of the scattered lights corresponding to the size of 0.294 µm can be very clearly discriminated from those corresponding to the size of 0.309 µm.

The thus obtained correlation is memorized in the memory 51.

Next, the function and effect of the particle counter 100 according to the present embodiment will be explained.

First, the particle counter 100 is arranged at a preset location inside the semiconductor processing unit 200. The ten laser fluxes L1, - - - , L10 are emitted from the laser source 10. The thus emitted laser fluxes are led into the projecting optical system 20, and projected as the light flux LO having almost the same light intensity distribution in the band-widthwise direction "d" in the gas stream passing area R. The intensity of the projected light flux LO is uniform in the advancing direction of the projected light LO. Therefore, the light intensity of the projected light LO is uniform over the entire gas stream passing area R.

If the particle J exists in the gas stream A, the projected light LO is irradiated upon the particle J when the particle J passes the gas stream passing area R. Then, the projected light flux LO is scattered with the particle J, and the scattered light K formed by scattering the projected light flux LO is led into a condenser 40 via the detection optical system 30. The condenser 40 detects the light intensity of the led scattered light K.

At that time, since the intensity of the projected light is uniform over the entire gas stream passing area R irrespective of the locations. Even if the particles J pass any parts of the gas stream passing area R, the detected intensities of the scattered lights are always constant so long as the sizes of the particles J are identical.

That is, the detected intensity of the scattered light does not depend upon the location of the gas stream passing area (position in the advancing direction and position in the band-widthwise direction) where the particle J passes.

On the other hand, the intensity of the scattered light K increases as the size of the particle J becomes greater.

The thus detected intensity of the scattered light K is inputted into the particle detector 50, which compares the inputted intensity of the scattered light with the threshold value memorized in the memory 51 and determines the size of the particle J corresponding to the intensity of the scattered light.

The particle detector 50 further counts the number of the particles having the determined size.

In the above, the determination of the sizes of the particles J and the counting of the number of the particles having said sizes are done for given time periods, thereby determining the sizes of the particles J having passed the gas stream passing area R and the number of the passed particles J with respect to each of the sizes. For example, the results are outputted to a monitor or a printer connected externally, and processing is terminated.

According to the thus constructed particle counter 100, the intensity in the widthwise direction "d" of the band-shaped projected light flux LO is almost uniform in the gas stream passing area R. Accordingly, even when the particles J pass arbitrary positions in the widthwise direction "d" of the gas steam passing area R, the detected intensities of the lights K scattered by the passed particles J are almost constant so long as the sizes of the particles are equal.

Therefore, dependency of the detected intensity of the scattered light in the gas stream passing area R upon the passing location (position in the light-advancing direction and position in the band-widthwise direction) can be avoided or reduced. Consequently, the correlation between the detected intensity of the scattered light K and the size of the passed particle J can be enhanced, so that the size of the particle having passed the band-shaped projected light flux can be accurately determined based on the detected intensity of the scattered light K.

Further, when the number of the passed particles for each of the sizes is to be counted, the accuracy of discriminating the sizes of the particles J is high, so that the number of the passed particles for each of the sizes can be accurately counted.

Further, since the correlation between the intensities of the scattered lights and the sizes of the particles J as memorized in the memory 51 possessed by the particle detector 50 can be accurately defined, the sizes of the particles can be assuredly and accurately determined in actual use based on the thus accurately defined correlation.

Furthermore, in order to achieve the uniformity of the intensity of the projected light flux LO, the particle counter 100 according to the present embodiment adopts the projecting optical system 20 in which the ten light fluxes L1, - - - , L10 emitted from the laser source 10 are passed through respectively different portions of the single lens (respectively different portions as viewed in radial direction orthogonal to the optical axis of the lens) to obtain light fluxes each having a smaller open angle, ten light fluxes L1, - - - , L10 are partially superposed upon each other between the adjacent light fluxes (L1 and L2, L2 and L3, L3 and L4, etc.), while the distance between the laser source 100 and the gas stream passing area R and/or the distance between the single lens and the gas stream passing area R can be adjusted. The particle monitoring apparatus is not limited to this embodiment. A projecting optical system may be adopted in which the ten light fluxes L1, - - - , L10 are collimated by means of the same number (ten) of lenses or fibers as that of the light fluxes, respectively, each of the light fluxes L1, - - - , LO is defocused, while a long distance between the gas stream passing area R and the ten lenses is ensured, and thereby the adjacent light fluxes are partially superposed upon each other.

According to the particle counter adopting such a projecting optical system, the respective one optical element (lens, fiber or the like) is provided for each of the light fluxes L1, - - - , L10. Therefore, the individual light fluxes can be easily adjusted with the corresponding optical elements, even if there are variations among the light fluxes L1, - - - , L10. Thus, the particle counter has the effect that adjustment can be easily performed to attain uniformity of the intensity of the projected light in the gas stream passing area R.

In the particle counter 100 according to the present embodiment, the light flux LO, which has the almost uniform projected light intensity in the band-widthwise direction "d", can be easily formed by emitting ten light fluxes L1, - - - , L10 in one-dimensionally arrayed fashion from the single laser source 10 and partially superposing the emitted light fluxes L1, - - - , L10 with the projecting optical system 20. The particle monitoring apparatus according to the present invention is not limited to one in which plural light fluxes are emitted from the single light source. The light source may be plural light sources each emitting one or more light fluxes.

The present invention is not limited to the single band-shaped projected light having the almost uniform intensity distribution in the widthwise direction as obtained by superposing plural light fluxes. A device may be used to form such a projected light by converting or rectifying the light intensity distribution almost uniform in the widthwise direction.

In the particle counter 100 according to the present embodiment, the particle detector 50 not only determines the sizes of the particles J but also counts the number of the particles J for each of the sizes. The particle monitoring apparatus according to the present invention is not limited to this embodiment. The particle detector 50 may not count the number of the particles J.

In such a particle monitoring apparatus, the sizes of the particles J can be accurately determined as in the case with the particle counter 100 of the above-mentioned embodiment.

Figure 5:
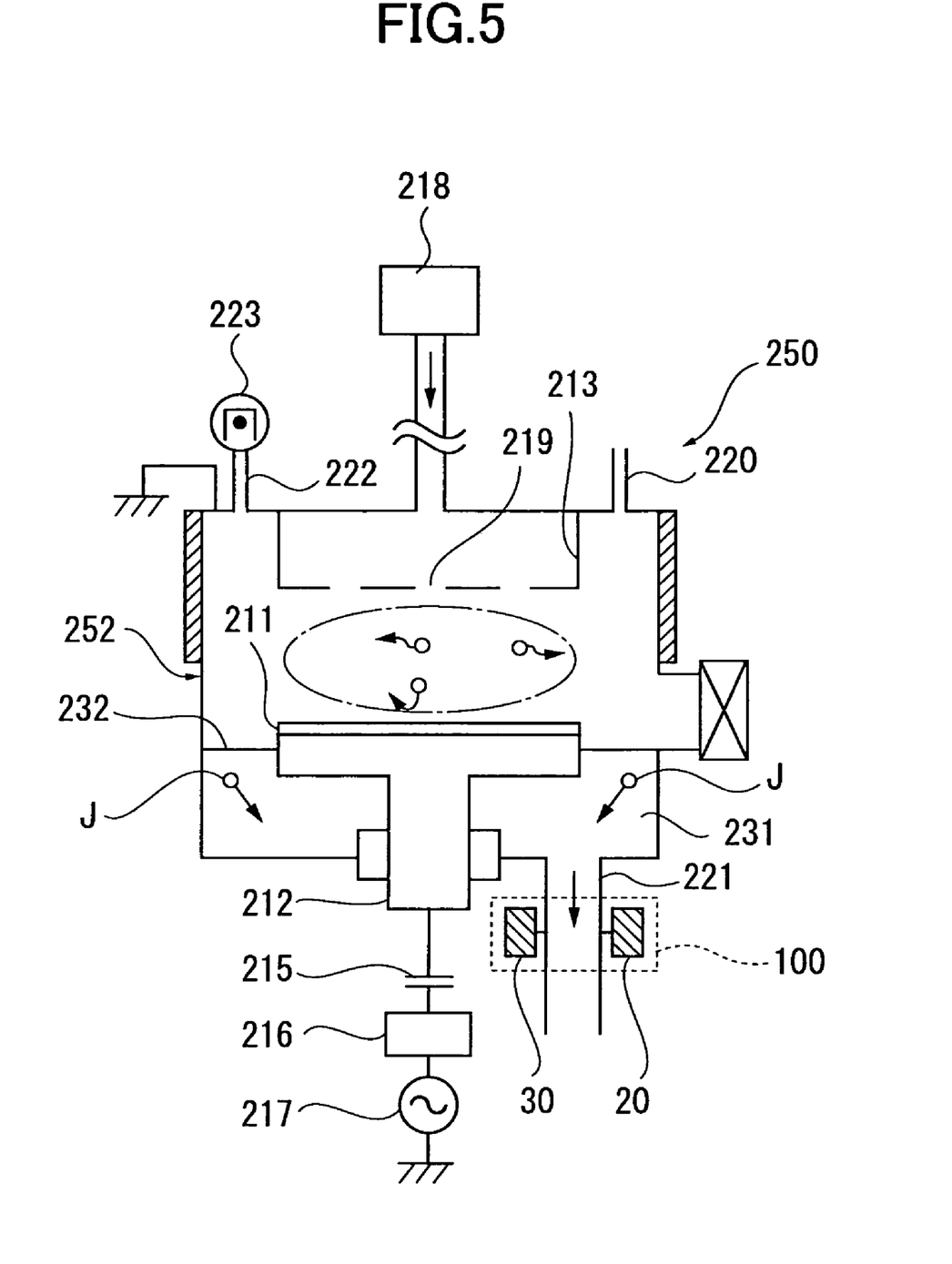
FIG. 5 is a schematic view showing a dry etching apparatus (vacuum processing apparatus) according to another embodiment of the present invention.

FIG. 5 shows a schematic construction of a dry etching apparatus 250 as one embodiment of the vacuum processing apparatus according to the present invention.

The etching apparatus 250 as shown is configured to etch a semiconductor wafer 211 (an object to be processed), and comprises a vacuum processing chamber 252 (container; processing chamber), an exhausting section (exhausting system) 231, a lower electrode 212, an upper electrode 213, a gas feeder (gas feeding means) 218, and the particle counter 100. The vacuum processing chamber 252 has an interior which can be held in a high vacuum atmosphere. The exhausting section 231 is provided under the vacuum processing chamber 252, and has an exhausting means such as a vacuum pump not shown for exhausting a gas inside the vacuum processing chamber 252 to outside. The lower electrode 212 is arranged in a lower portion of the vacuum processing chamber 252, and serves as a placing table on which the wafer 211 is placed. The upper electrode 213 is arranged opposed to the lower electrode 212 inside the vacuum processing chamber 252. The gas feeder 218 feeds a given gas to the vacuum processing chamber 252 for etching. The particle counter 100 monitors the particles J in the gas stream passing the exhausting section 231.

Herein, a high frequency power source 217 is connected to the lower electrode 212 via a blocking condenser 215 and a high frequency matching circuit 216. The upper electrode 213 is provided with blow-out openings 219 for blowing out the gas send out from the gas feeder 218.

In the vacuum processing chamber 252 are further provided an exhausting plate 232 (baffle plate or the like) to partition a plasma space of the vacuum processing chamber 252 from an exhausting space of the exhausting section 231, an introduction pipe 220 to introduce a gas into the vacuum processing chamber 252, an exhausting opening 221 connected to an exhausting unit not shown, and a pressure gauge 223 to measure the internal pressure of the vacuum processing chamber 252 via a pressure measuring opening 222.

According to the thus constructed dry etching apparatus 250, the wafer 211 is subjected to an etching cycle on the lower electrode 212. Thereby, particles J are gradually formed and suspended inside the vacuum processing chamber 252.

Thereafter, the gas inside the vacuum processing chamber 252 is depressurized by exhausting the gas therein by means of the exhausting unit not shown, and a given gas is introduced into the vacuum processing chamber 252 through the introduction pipe 220. Thereby, the gas stream is formed to pass the exhausting section 231, so that the particles J inside the vacuum processing chamber 252 are passed through the exhausting section 231 together with this gas stream.

The particle counter 100 shown in FIG. 1 monitors the above particles J with respect to the gas stream passing the exhausting section 231, and determines the sizes and the numbers of the particles J passing the exhausting section 231 with high accuracy.

The detected results are inputted to a control unit (controller) not shown of the dry etching apparatus 250, and the control unit controls the operations of the gas feeder 218, the exhausting section 231, the electrodes 212, 213, etc. according to a preset processing procedure corresponding to the detected results.

Thereby, the dry etching apparatus 250 of the present embodiment can realize an appropriate operation state according to the existing state of the particles J inside the vacuum processing chamber 250.

What is claimed is:

1. A particle monitoring apparatus comprising:
    a light source configured to emit plural light fluxes in at least a one-dimensional array having a given intensity;
    a projecting optical system configured to convert the plural light fluxes in the at least one-dimensional array emitted from the light source into a band-shaped light flux, to lead the light flux into a flow passage of a given gas stream so that the given gas stream passes the band-shaped light flux, and to partially superpose the plural light fluxes in the at least one-dimensional array emitted from the light source to form a substantially uniform light intensity distribution of the band-shaped light flux in a widthwise direction;
    a light detector configured to detect intensity of light;
    a detecting optical system configured to lead light scattered by particles contained in the gas stream and passing the light flux to the light detector; and
    a particle detector configured to determine sizes of the particles passing the light flux based on intensities of the scattered lights detected by the light detector and to count the number of the particles passing the light flux for a given period.

2. The particle monitoring apparatus set forth in claim 1, wherein the projecting optical system comprises plural optical systems provided in a number corresponding to that of the plural light fluxes emitted from the light source and adapted for leading the plural light fluxes, respectively.

3. A particle monitoring apparatus comprising:
    a light source configured to emit a light having a given intensity;
    a projecting optical system configured to convert the light emitted from the light source into a band-shaped light flux and to lead the light flux onto a flow passage of a given gas stream so that the given gas stream may pass the band-shaped light flux;
    a light detector configured to detect the intensity of the light;
    a detecting optical system configured to lead the light scattered by particles contained in the gas stream and passing the light flux to the light detector; and
    a particle detector configured to determine sizes of the particles passing the light flux based on intensities of the scattered lights detected by the light detector and to count the number of the particles passing the light flux for a given period, wherein
    the light intensity of the band-shaped light flux is set to have an almost uniform distribution in a horizontal direction, and
    the light source comprises at least two light sources, and the projecting optical system is configured to divide the light flux emitted from each of the light sources into plural light fluxes, to make divided light fluxes of one light source adjacent to those of corresponding different light source(s) to partially superpose the adjacent divided light fluxes with each other and to make almost uniform the light intensity distribution of the band-shaped light flux in the band-widthwise direction.

4. The particle monitoring apparatus set forth in claim 1, wherein the light source comprises at least two light sources, and the projecting optical system is configured to divide the light flux emitted from each of the light sources into plural light fluxes, to make divided light fluxes of one light source adjacent to those of corresponding different light source(s) to partially superpose the adjacent divided light fluxes with each other and to make almost uniform the light intensity distribution of the band-shaped light flux in the band-widthwise direction.

5. The particle monitoring apparatus set forth in claim 1, wherein the particle detector comprises a memorizing unit configured to preliminarily memorize correlation between the sizes of the particles passing the gas stream passing area and the intensities of the scattered lights detected by the light detector, and the correlation memorized in the memorizing unit is defined by successively passing plural kinds of test particles each having a different known size through the gas stream passing area, independently detecting the intensities of the scattered lights with the light detector when each of the plural kinds of test particles pass the gas stream passing area, determining a frequency distribution in the light intensities detected by the light detector, determining the correlation between the size of each of the plural kinds of the particles and the detected light intensities of the scattered lights by the particles having such sizes based on the frequency distribution, replacing one kind of the test particles by another kind of the test particles having a known different size and passing said another kind of the test pieces through the gas stream passing area and determining the intensities of the scattered lights when the said test particles passed, and determining the correlation between the size of another kind of the test particles and the detected light intensities of the scattered lights, and repeating the above latter step.

6. A particle monitoring apparatus comprising:
    a light source configured to emit plural light fluxes in at least a one-dimensional array having a given intensity;
    a projecting optical system configured to convert the plural light fluxes in the at least one-dimensional array emitted from the light source into a band-shaped light flux, to lead the light flux into a flow passage of a given gas stream so that the given gas stream passes the band-shaped light flux, and to partially superpose the plural light fluxes in the at least one-dimensional array emitted from the light source to form a substantially uniform light intensity distribution of the band-shaped light flux in a widthwise direction;
    a light detector configured to detect intensity of light;
    a detecting optical system configured to lead light scattered by particles contained in the gas stream and passing the light flux to the light detector; and
    a particle detector configured to determine sizes of the particles passing the light flux based on intensities of the scattered lights detected by the light detector, wherein the light intensity of the band-shaped light flux is set to have an almost uniform distribution in a horizontal direction.

7. A vacuum processing apparatus, which is configured to perform a given processing upon an object disposed in a given vacuum atmosphere inside a vessel, said vacuum processing apparatus including the particle monitoring apparatus set forth claim 1.

8. A vacuum processing apparatus, which is configured to perform a given processing upon an object disposed in a given vacuum atmosphere inside a vessel, said vacuum processing apparatus comprising the particle monitoring apparatus set forth claim 3.

9. A vacuum processing apparatus, which is configured to perform a given processing upon an object disposed in a given vacuum atmosphere inside a vessel, said vacuum processing apparatus comprising the particle monitoring apparatus of claim 1 in an exhaust section.

10. A vacuum processing apparatus, which is configured to perform a given processing upon an object disposed in a given vacuum atmosphere inside a vessel, said vacuum processing apparatus comprising the particle monitoring apparatus of claim 3 in an exhaust section.

* * * * *